United States Patent [19]

Salerno

[11] Patent Number: 5,337,735
[45] Date of Patent: Aug. 16, 1994

[54] FIBER-LIGHTED STYLET

[76] Inventor: Albert Salerno, 13007 E. Park Ave., Santa Fe Springs, Calif. 90670

[21] Appl. No.: 998,396

[22] Filed: Dec. 28, 1992

[51] Int. Cl.⁵ ............................................. A61B 1/06
[52] U.S. Cl. ...................................... 128/11; 128/23; 128/6; 385/117
[58] Field of Search .................. 128/10, 11, 6, 16, 11, 128/7, 22, 23; 385/115, 116, 117

[56] References Cited

U.S. PATENT DOCUMENTS

| D. 297,363 | 8/1988 | Salerno et al. ................ D24/18 |
| 543,616 | 7/1895 | Dow ................................. 128/10 |
| 2,289,226 | 7/1942 | Von Foregger ................. 128/16 |
| 3,281,637 | 10/1966 | Hultquist . | |
| 3,699,950 | 10/1972 | Humphrey, Jr. et al. ......... 128/23 |
| 3,739,769 | 6/1973 | Kaye ................................ 128/6 |
| 3,776,222 | 12/1973 | Smiddy ........................ 385/117 X |
| 3,809,072 | 5/1974 | Ersek et al. ..................... 128/23 |
| 3,941,121 | 3/1976 | Olinger et al. .................... 128/6 |
| 3,986,854 | 10/1976 | Scrivo et al. ................... 65/4 R |
| 4,273,112 | 6/1981 | Heine et al. .................... 128/11 |
| 4,320,745 | 3/1982 | Bhitiyakul et al. .......... 128/16 X |
| 4,406,280 | 9/1983 | Upsher ........................... 128/11 |
| 4,583,527 | 4/1986 | Musicant et al. .............. 128/11 |
| 4,924,855 | 5/1990 | Salerno et al. ................. 128/11 |
| 5,131,380 | 7/1992 | Heller et al. ............... 128/11 X |
| 5,183,031 | 2/1993 | Rossoff ....................... 128/11 X |

Primary Examiner—Richard J. Apley
Assistant Examiner—Beverly A. Meindl
Attorney, Agent, or Firm—Trask, Britt & Rossa

[57] ABSTRACT

Disclosed is a fiber-illuminated stylet or probe useful for among other things in assisting in the performance of intubations. The stylet has a handle having a light source from which extends an encased, malleable fiber-optic cable capable of transmitting light to the local area to be seen (e.g. in the vicinity of the epiglottis).

12 Claims, 2 Drawing Sheets

FIBER-LIGHTED STYLET

TECHNICAL FIELD

The present invention relates to medical or dental instruments generally, and to an illuminable stylet specifically.

BACKGROUND

During a medical intubation procedure, a tube is inserted into an orifice or hollow organ such as the larynx to allow for the administration of gases or to admit air. Unfortunately, the procedure sometimes goes amiss, and the tube is inserted into the wrong orifice (e.g. into the digestive rather than the respiratory tract).

Although illuminated laryngoscopes which might help to alleviate this situation are available (see, e.g. U.S. Pat. No. 3,986,854 to Scrivo et al., U.S. Pat. No. 4,583,527 to Musicant et al., U.S. Pat. No. Des. 297,363 to Salerno et al., and U.S. Pat. No. 4,924,855 to Salerno et al.), the amount of illumination is somewhat inherently limited by the length of the laryngoscope blade.

It would be an improvement in the art if a device were available for safely illuminating an intubation procedure, especially in the lower part of the pharynx.

DISCLOSURE OF THE INVENTION

The invention includes a fiber-lighted stylet used to illuminate an intubation procedure more safely. A stylet according to the invention includes a handle from which extends a flexible fiber-optic cable (or cables) encased within a malleable material. The handle is associated with a light source for transmission of light through the encased fiber-optic cable to the tip of the cable. The distal end of the encased cable is freely moveable by manual manipulation, but once placed into a position, has the characteristic of maintaining its selected conformation until later manipulation by a user's (e.g. an anesthesiologist's) hands. The stylet has the advantages of being able to illuminate the lower portions of the pharynx during an intubation or similar procedure, while the use of a fiber-optic cable for light transmission allows the light source to be securely attached to the handle and maintained safely outside of the subject's body.

BRIEF DESCRIPTION OF THE FIGURES

In the drawings, which depict presently preferred embodiments of the invention and in which like reference numerals refer to like parts in different views.

BEST MODE OF THE INVENTION

Figures 1, 2:
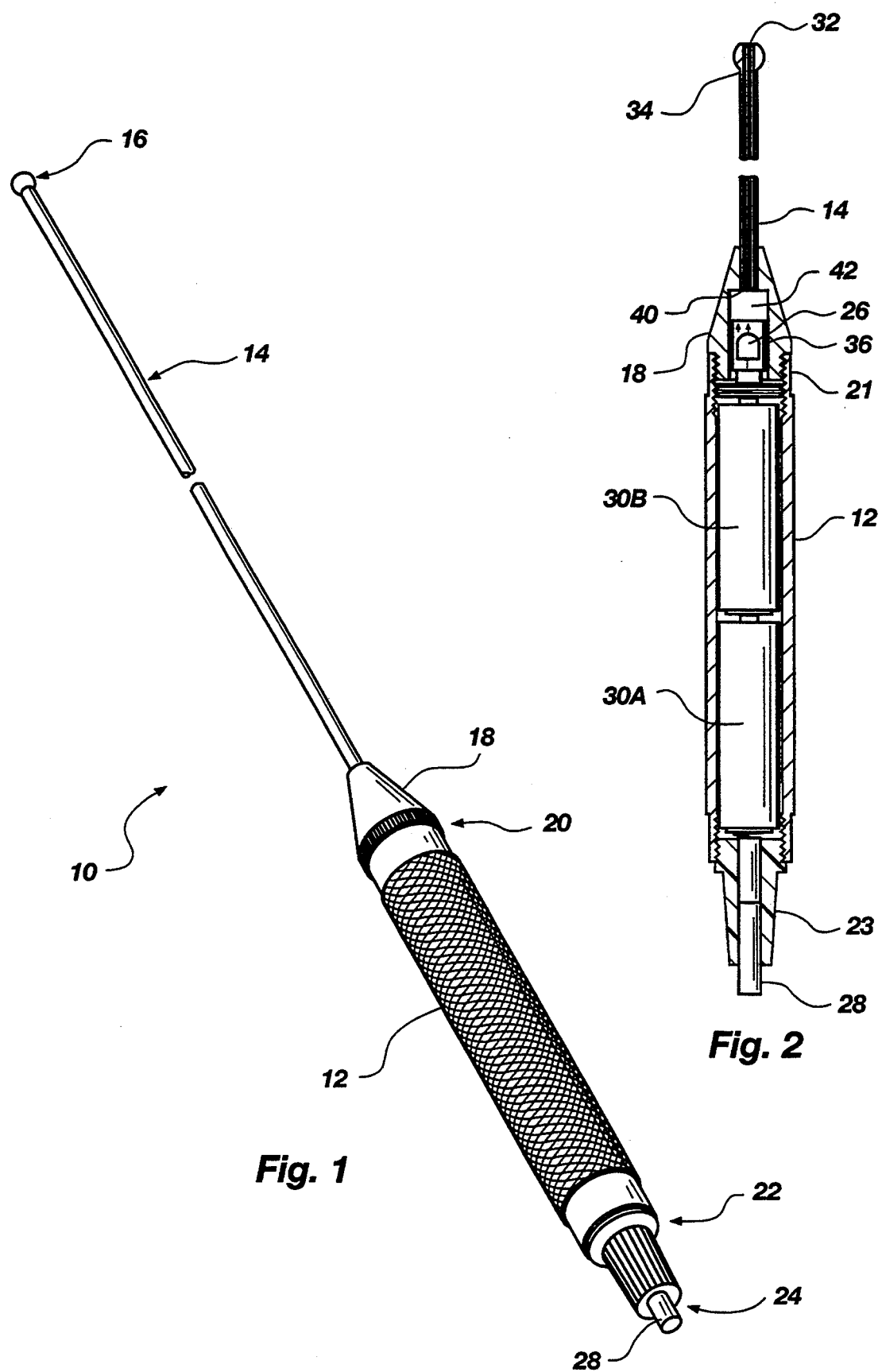
FIG. 1 is a perspective view of a preferred instrument in accordance with the invention.
FIG. 2 is a cut-away view of a preferred instrument according to the invention.

As shown in FIG. 1, a preferred device according to the invention, generally 10, has a tubular handle 12 having a length varying from about eight to about fifteen centimeters (cm). The handle 12 is associated with an encased fiber-optic cable or bundle of cables 14 extending from the handle 12 to an end point 16.

The handle is sized to fit within the hand of the user, and preferably has a diameter of between sixteen and twenty millimeters. In one preferred embodiment, the handle is made of stainless steel, although other materials, especially those capable of conducting a current, may be used. Materials useful for making the handle include: brass, aluminum, plastic, and stainless steel. The exterior surface of the handle may be gnarled or rough in order to provide a more secure grip for a user.

The encased cable 14 extending from the handle is preferably capable of being removed from and reassociated with the handle 12, although it may also be permanently affixed to the handle especially in the case of disposable instruments. Various encased cables of different lengths may be used with one handle. The instrument depicted in FIGS. 1 & 2 has a concave cowl 18 having outer threads which co-act with internal threads 21 on the distal end, generally 20, of the handle 12 (FIG. 2). The encased fiber optic cable extends through the concave threaded cowl 18 and preferably extends a predetermined length to its end 16.

On the handle's proximal end, generally 22, is preferably a switch 24. This switch 24 controls the illumination of a light source 26 preferably mounted on the distal end of the handle underneath the threaded cowl 18 (FIG. 2). In the depicted embodiment, the switch 24 has a base 23 made of an insulating material (e.g. plastic), and, similar to a flashlight, when the button 28 is pressed, a circuit is completed between the batteries 30A, 30B and the light source 26, using a electrically conducting handle 12 to complete the circuit. An ideal switch for use with the depicted device is one which turns on and off or one which pushes on and pulls off. Readily commercially available switches may be used or adapted for use.

The fiber optic cable 32 is flexible at room temperature and is of a diameter sufficient to transmit light for illuminating a local area. It can be a single cable having a diameter of from two to four millimeters, preferably 3.0 to 3.1 mm, or may be a bundle of smaller cables having a similar diameter. The encased cable 14 will typically have a length ranging from twenty to forty-five centimeters, preferably twenty-five to thirty-three centimeters, although practically any chosen length can be used. The thickness of the casing itself will vary from 0.45 to 0.9 mm, and will be sufficiently thick to be malleable, but somewhat rigid. The material 34 encasing the cable or cables is a material, malleable at room temperature at the thickness chosen, such as stainless steel, brass or malleable iron. Once bent into its desired conformation, the encased cable 14 will generally remain in that position until it is again manipulated by the user to a different position. The casing 34 coats or encases the fiber optic cable along its longitudinal portion like a pipe, and has two open ends 32, 40 to permit the passage of light from the light source 26 through the encased cable 14 to the end point 16. Such an arrangement allows the instrument to project light out into a local area adjacent (within at least 0.5 cm directly in front of) the end point. The fiber-optic cable can be slipped into the tubular encasing material.

Fiber optic cables suitable for use with the invention can be purchased from Amtec Medical Products.

The light source can be a lamp, bulb, or similar device. In the depicted device (FIG. 2), the bulb (e.g. a 2.7 volt bulb from Amtec Medical Products) is powered by two 1.5 volt AA batteries 30A, 30B. The light from the light source projects up a small cylinder 36 to the bottom 40 of the encased cable 14.

In another embodiment (not depicted) the light source is light transmitted (e.g. by a fiber-optic cable)

from a source distinct from the handle to the bottom 40 of the encased cable.

Whatever the light source, the bottom 40 of the encased cable constitutes one of the two optical faces. Accordingly the light source is chosen to be of a sufficient power to transmit light up through the optical face and cable and the strength of light source required will depend somewhat on the transmission capability of the fiber 32.

Figure 3:
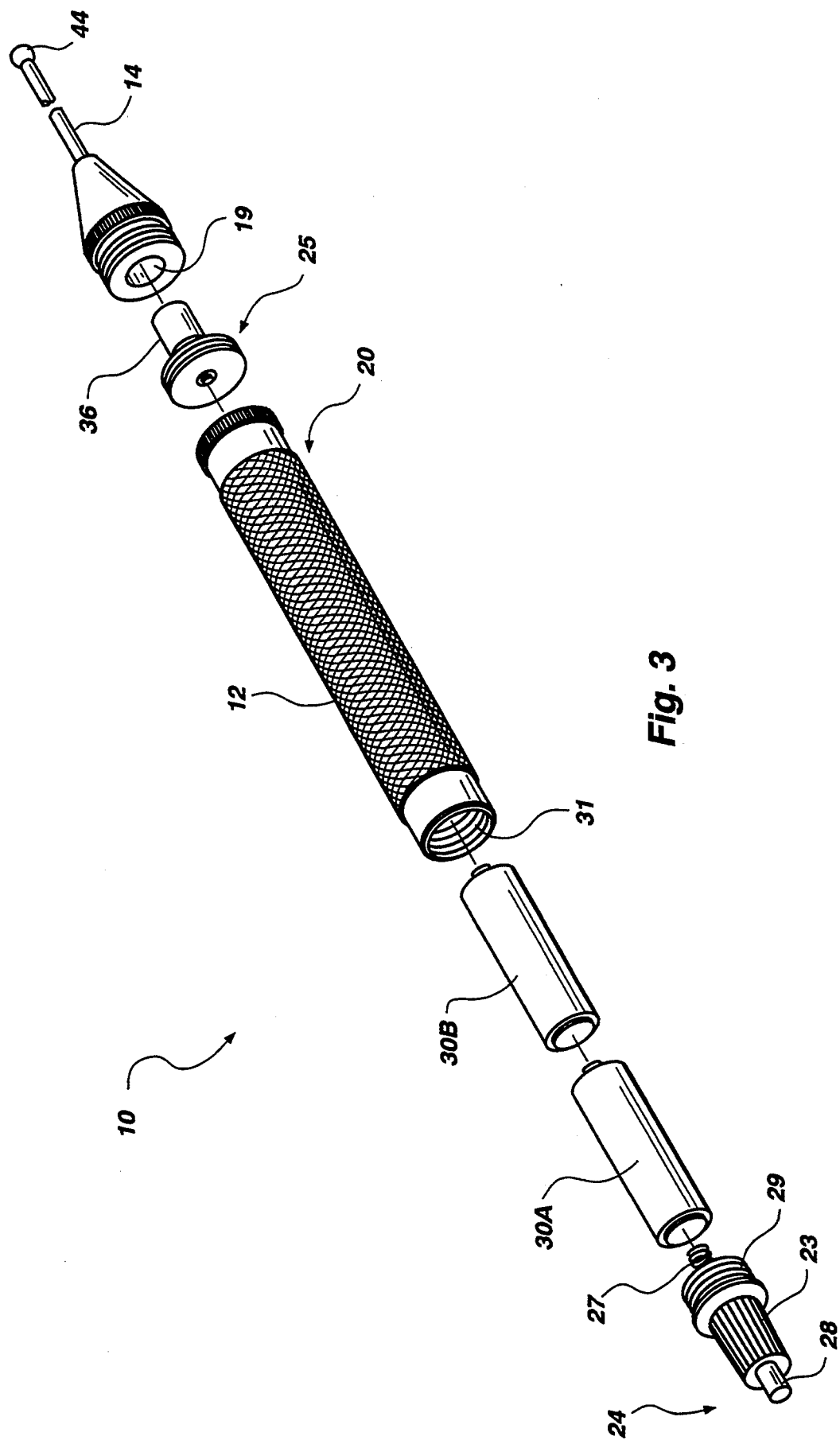
FIG. 3 is a side-view of a disassembled preferred instrument according to the invention.

FIG. 3 depicts a preferred embodiment of the device 10 disassembled. Starting from the proximal end of the device 10, a switch 24 is seen having a button 28, a plastic base 23 and a spring 27. The base 23 has threads 29 which interact with threads 31 inside handle 12. The handle is of a sufficient diameter to contain two batteries 30A, 30B for powering the light source. The light source is placed within a second base 25 having a bulb encased within a cylindrical portion 36. The second base 25 has threads which interact with the threads 21 if the distal end of the handle. The concave cowl 18 is placed on the distal portion 20 of the handle and also interacts with those threads 21 to ensure a secure arrangement. The cowl has a cavity 19 within which the cylindrical portion 36 slidably fits, leaving a small gap 42 best seen in FIG. 2. The encased cable extends for as long as desired, and preferably ends with a dull bulbous end 44. The dull bulbous end 44 is preferably made with a thickening of the casing material, and it acts to help prevent injuries to the subject undergoing the probe procedure.

For use in an intubation procedure, the instrument is preferably first sterilized, e.g. by autoclaving, before use. The light source of the instrument of FIGS. 1-3 is then illuminated. The encased cable is bent to the desired conformation. It is then placed into the mouth of the subject and directed down to the lower pharynx to illuminate the local area around the epiglottal area properly. The procedure may be performed with the aid of a laryngoscope. The intubation device is then directed down the subject's pharynx for proper placement.

Once the device according to the invention has been seen by one of skill in the art, methods and materials for making it will become readily apparent. For instance, the handle and cowl may be machined from commonly available metals or other materials. Batteries, fiber-optic cable, spring, light bulb, and switch may be purchased. The bulbous end portion of the casing may be welded. The ends of the fiber optic cable or cables are preferably polished to form a better optical face.

Although the invention has been described with regard to certain preferred embodiments, the scope of the invention is to be defined by the appended claims.

What is claimed is:

1. An instrument for illuminating a local area comprising:
    a handle having proximal and distal ends, the handle's distal end having a light source associated therewith;
    a fiber optic cable having first and second ends, said fiber optic cable being flexible and further being removably attached at its first end to the handle's distal end and extending away from the light source and said distal and proximal ends;
    a malleable casing partially encasing said fiber optic cable, said malleable casing open on both ends to allow light to pass from said light source through said encased fiber optic cable to illuminate a local area adjacent the second end of the fiber optic cable; and
    a concave cowl in threaded attachment with the handle's distal end for detachably connecting the first end of said fiber optic cable to the distal end of the handle, wherein said light source is positioned within a cylindrical protective portion enclosed by said concave cowl.

2. The instrument of claim 1 further comprising:
    a switch, associated with the handle, for controlling illumination and extinguishment of the light source.

3. The instrument of claim 2, wherein said switch is placed at the proximal end of the handle.

4. The instrument of claim 1 wherein an energy source for said light source is enclosed within the handle.

5. The instrument of claim 1 wherein said encased fiber optic cable has a bulbous end.

6. The instrument of claim 1 wherein the light source is a light bulb.

7. The instrument of claim 4 wherein the handle is made of an electrically conducting material, and said handle acts to complete a circuit between the energy source and the light source.

8. An improvement in a medical intubation procedure, the improvement comprising using an instrument for illuminating the procedure, wherein the instrument comprises:
    a handle having proximal and distal ends, the handle's distal end having a light source associated therewith;
    a fiber optic cable having first and second ends, said fiber optic cable being flexible and attached at its first end to the handle's distal end and extending longitudinally away from the light source and said distal and proximal ends;
    a malleable casing at least partially encasing said fiber optic cable, said malleable casing open on both ends to allow fight to pass from said light source through said encased fiber optic cable to illuminate a local area proximate the area to be intubated; and
    a concave cowl in threaded attachment with the handle's distal end for detachably connecting the first end of said fiber optic cable to the distal end of the handle, wherein said light source is placed within a cylindrical protective portion enclosed by said concave cowl.

9. The improvement of claim 8 wherein the length of the encased fiber optic cable is from twenty to forty-five centimeters.

10. The improvement of claim 8 wherein the instrument further comprises:
    a switch for controlling illumination and extinguishment of the light source, said switch positioned at the handle's proximal end.

11. The improvement of claim 8 wherein the light source is a light bulb.

12. An instrument for illuminating a local area comprising:
    a handle, made of an electrically conductive material, having proximal and distal ends, the handle's distal end having a light source associated therewith, said handle further containing an energy source for said fight source, said handle acting to selectively complete a circuit between the energy source and the light source;
    a fiber optic cable having first and second ends, said fiber optic cable being flexible and further being removably attached at its first end to the handle's distal end and extending away from the fight source and said distal and proximal ends;

a malleable casing partially encasing said fiber optic cable, said malleable casing open on both ends to allow light to pass from said light source through said encased fiber optic cable to illuminate a local area adjacent the second end of the fiber optic cable; and means for detachably connecting the first end of said fiber optic cable to the distal end of the handle.

* * * * *

UNITED STATES PATENT AND TRADEMARK OFFICE
CERTIFICATE OF CORRECTION

PATENT NO. : 5,337,735

DATED : August 16, 1994

INVENTOR(S) : Salerno

It is certified that error appears in the above-indentified patent and that said Letters Patent is hereby corrected as shown below:

In Column 4, line 39, change "fight" to --light--; and

In Column 4, line 64, change "fight" to --light--; and

In Column 5, line 2, change "fight" to --light--.

Signed and Sealed this

Eighth Day of November, 1994

Attest:

BRUCE LEHMAN

*Attesting Officer*  *Commissioner of Patents and Trademarks*